United States Patent
Lin et al.

(10) Patent No.: US 10,048,189 B2
(45) Date of Patent: Aug. 14, 2018

(54) TEMPERATURE COMPENSATION FOR PARTICULATE MATTER SENSOR REGENERATION

(71) Applicant: Cummins IP, Inc., Columbus, IN (US)

(72) Inventors: Xiao Lin, Columbus, IN (US); Archana Chandrasekaran, Columbus, IN (US); Jinqian Gong, Columbus, IN (US)

(73) Assignee: CUMMINS IP, INC., Columbus, IN (US)

( * ) Notice: Subject to any disclaimer, the term of this patent is extended or adjusted under 35 U.S.C. 154(b) by 251 days.

(21) Appl. No.: 14/968,079

(22) Filed: Dec. 14, 2015

(65) Prior Publication Data

US 2016/0097704 A1   Apr. 7, 2016

Related U.S. Application Data

(62) Division of application No. 14/069,081, filed on Oct. 31, 2013, now Pat. No. 9,234,805.

(51) Int. Cl.
 *G01D 15/06* (2006.01)
 *G01N 15/06* (2006.01)
 (Continued)

(52) U.S. Cl.
 CPC ..... *G01N 15/0656* (2013.01); *F02D 41/1466* (2013.01); *F02D 41/1494* (2013.01);
 (Continued)

(58) Field of Classification Search
 CPC .......... G01K 7/22; G01R 27/08; G01D 15/06
 See application file for complete search history.

(56) References Cited

U.S. PATENT DOCUMENTS 5,214,267 A  5/1993 Hoshi et al.
6,307,187 B1 10/2001 Peter et al.
(Continued)

FOREIGN PATENT DOCUMENTS

DE  10 2008 004 210  12/2009
DE  1020080 04 210   12/2009
(Continued)

OTHER PUBLICATIONS

Extended European Search Report issued in European Application No. 14188263.9, dated Mar. 17, 2015.
(Continued)

*Primary Examiner* — Robert R Raevis
(74) *Attorney, Agent, or Firm* — Foley & Lardner LLP (57) ABSTRACT

The present disclosure relates to a controller apparatus for regenerating a particulate matter sensor. The controller apparatus includes a sensing module configured to detect a soot loading on a particulate matter sensor and generate a regeneration request indicating a desired regeneration temperature and a heating module configured to receive the regeneration request and send a heating command signal to a heating element based on the regeneration request. The controller apparatus also includes an electrical resistance module configured to detect an electrical resistance in the heating element, a calibration module configured to determine an actual temperature of the heating element based on a resistance-to-temperature model, and a temperature feedback module configured to modify the heating command signal according to the difference between the desired regeneration temperature and the actual temperature.

19 Claims, 9 Drawing Sheets

(51) Int. Cl.
  *G01K 7/22* (2006.01)
  *G01R 27/08* (2006.01)
  *G05D 23/24* (2006.01)
  *G01K 15/00* (2006.01)
  *F02D 41/14* (2006.01)

(52) U.S. Cl.
  CPC ............ *G01K 7/22* (2013.01); *G01K 15/005* (2013.01); *G01R 27/08* (2013.01); *G05D 23/2401* (2013.01); *F01N 2560/05* (2013.01); *F01N 2560/20* (2013.01)

(56) References Cited

U.S. PATENT DOCUMENTS

| | | |
|---|---|---|
| 6,850,859 B1 | 2/2005 | Schuh |
| 7,891,177 B2 | 2/2011 | Ammineni et al. |
| 8,182,665 B2 | 5/2012 | Dorfmueller et al. |
| 8,249,827 B2 | 8/2012 | Nelson et al. |
| 8,281,576 B2 | 10/2012 | Parnin |
| 2005/0263397 A1 | 12/2005 | Yasui et al. |
| 2009/0084771 A1* | 4/2009 | Nomura ............ G05D 23/1913 219/263 |
| 2011/0283773 A1 | 11/2011 | Suzuki |
| 2012/0031078 A1 | 2/2012 | Sakamoto et al. |
| 2012/0125081 A1 | 5/2012 | Yadav et al. |
| 2012/0186230 A1 | 7/2012 | Yahata et al. |
| 2012/0186330 A1 | 7/2012 | Ueno et al. |

FOREIGN PATENT DOCUMENTS

| | | |
|---|---|---|
| EP | 1 921 430 | 5/2008 |
| EP | 2 645 073 | 10/2013 |
| WO | WO-2012/162685 | 11/2012 |

OTHER PUBLICATIONS

Third Party Observations issued in European Patent Application No. EP14188263.9, dated Oct. 28, 2016.

H.W. Cory: "Proposed Symbols and Terms for Feedback Control Systems," Electrical Engineering, vol. 70, No. 10, Oct. 1, 1951, pp. 905-909.

Communication issued by the European Patent Office for European Patent Application No. 14 188 263.9, dated Nov. 23, 2016, 6 pages.

The extended European Search Report issued in European Application No. 14188263.9, dated Mar. 17, 2015.

\* cited by examiner

TEMPERATURE COMPENSATION FOR PARTICULATE MATTER SENSOR REGENERATION

CROSS-REFERENCE TO RELATED PATENT APPLICATIONS

This application is a divisional of U.S. patent application Ser. No. 14/069,081, filed Oct. 31, 2013, which is incorporated herein by reference in its entirety.

FIELD

This disclosure relates to particulate matter sensors and more particularly relates to temperature compensation during the regeneration of particulate matter sensors.

BACKGROUND

Various components and devices are employed in conventional exhaust gas aftertreatment systems to reduce the emission of harmful pollutants. One specific component that is often included in exhaust gas aftertreatment systems is a particulate matter filter. Particulate matter filters trap pollutants, such as unburned hydrocarbons, soot, and other particulates. As particulates accumulate on the filter, the flow path of exhaust gas through the filter becomes more restrictive, thus increasing the pressure drop across the filter and increasing backpressure on the engine. In order to determine when a particulate filter requires cleaning (also known as regeneration or reactivation), conventional engine systems often monitor the pressure drop across the particulate filter and initiate a regeneration procedure when the pressure reaches a certain level.

However, if a particulate filter in an exhaust stream has cracks or leaks, the pressure measurement will not accurately reflect the level of particulate loading on the filter. Further, as emissions standards become more stringent, pressure monitoring control systems are generally inadequate in accurately determining the level and degree of particulate accumulation on a filter. Conventional solutions to this problem include implementing a particulate matter sensor in the exhaust gas flow. Particulate matter sensors, used to measure soot and other particulate matter, typically consist of a non-conductive substrate, most often alumina, with a screen-print pattern of conductive material. The conductive material, which may be a precious metal in order to withstand the temperature of exhaust gas streams, functions as a sensing element to determine the level of particulate accumulation. In some instances the particulate matter sensor will also have a heating element to heat the soot sensor during a sensor regeneration procedure.

The sensing element (conductive material) of the particulate matter sensor generally has two electrodes with inter-digitized 'fingers' that maximize a perimeter between the two electrodes. When soot from the exhaust gas is deposited onto the sensor, the carbon component of the soot creates a high resistance short between the electrodes, which effectively lowers the resistance. The more soot that accumulates on the sensing element, the lower the resistance. Once a predetermined amount of soot is on the sensing element, it is often desirable to clean off the soot from the sensor. Accordingly, the heating element on the particulate matter sensor may be activated to oxidize the soot and regenerate the sensor. The temperature of the heating element is often an important factor in the sensor regeneration process. If the regeneration temperature is too low, then not enough soot will be removed from the sensor or the sensor regeneration procedure will take an excessive amount of time. If the temperature is too high, the various components of the sensor may be damaged due to the high temperatures. While conventional solutions involve implementing a temperature sensor to monitor the temperature of the heating element, the addition of temperature sensors adds cost and complexity to the aftertreatment system. Further, some temperature sensors fail to accurately account for how the fluctuating exhaust gas conditions affect the accuracy of the temperature detection.

SUMMARY

The subject matter of the present disclosure has been developed in response to the present state of the art, and in particular, in response to the limitations of conventional particulate matter sensors. Specifically, conventional particulate matter sensors fail to effectively and efficiently monitor and control the temperature of the heating element. Accordingly, the subject matter of the present disclosure has been developed to provide an apparatus, system, and method for using the heating element itself as a thermistor to detect the temperature of the heating element. Further, due to the part-to-part variation in the heating element components and the fluctuating condition of the exhaust gas, the subject matter of the present disclosure also relates to compensating the temperature feedback control to account for these disturbances. Therefore, the subject matter of the present disclosure relates to providing temperature feedback control and temperature calibration in the particulate matter sensor regeneration procedure in order to overcome at least some of the above-discussed shortcomings of the prior art.

The present disclosure relates to a controller apparatus for regenerating a particulate matter sensor. The controller apparatus includes a sensing module configured to detect a soot loading on a particulate matter sensor and generate a regeneration request indicating a desired regeneration temperature and a heating module configured to receive the regeneration request and send a heating command signal to a heating element based on the regeneration request. The controller apparatus also includes an electrical resistance module configured to detect an electrical resistance in the heating element, a calibration module configured to determine an actual temperature of the heating element based on a resistance-to-temperature model, and a temperature feedback module configured to modify the heating command signal according to the difference between the desired regeneration temperature and the actual temperature.

In one embodiment, the electrical resistance is detected by measuring a response voltage and converting the response voltage into the electrical resistance. The controller apparatus may also further include a signal adjustment module configured to convert the heating command signal to an adjusted heating command signal, wherein the response voltage in the heating element has a steady-state portion. In one implementation, the net power delivered to the heating element remains unchanged when the heating command signal is converted to the adjusted heating command signal. For example, the adjusted heating command signal may include pulse width modulation techniques and the pulses, at least the pulses for which the response voltage is being measured, may have a duty cycle of at least 30%. The calibration module may further include a thermistor sub-module configured to generate a resistance-to-temperature response model based on known temperature conditions of a heating element and an exhaust sub-module configured to adjust the resistance-to-temperature response model based on dynamic exhaust flow information. In another embodiment, the thermistor sub-module may be configured to generate the resistance-to-temperature response model based on an exhaust temperature upstream of the particulate matter sensor or on ambient temperature in a short period after engine key-on or engine key-off.

The present disclosure also relates to a method for regenerating a particulate matter sensor. The method includes sensing a soot loading on a particulate matter sensor and powering a heating element to heat the particulate matter sensor to a desired regeneration temperature to oxidize at least a portion of the soot loading. Further, the method includes detecting an electrical resistance in the heating element and correlating the electrical resistance of the heating element to an actual temperature of the heating element based on a resistance-to-temperature model. Still further, the method includes modifying the power delivered to the heating element according to the difference between the desired regeneration temperature and the actual temperature of the heating element. The electrical resistance may be detected by measuring a response voltage and converting the response voltage into the electrical resistance. Also, the heating command signal may be converted to an adjusted heating command signal that produces a response voltage in the heating element that has a steady-state portion.

In one embodiment, the method for regenerating a particulate matter sensor includes correlating the electrical resistance of the heating element to an actual temperature of the heating element. This correlation is performed by collecting electrical resistance data when the heating element is at a known temperature condition, generating a resistance-to-temperature model for the heating element based on the electrical resistance data, and determining the actual temperature of the heating element based on the resistance-to-temperature model.

Also disclosed in the present disclosure is a system for regenerating a particulate matter sensor. The system includes a particulate matter sensor that has a sensing element and a heating element. The system further includes a sensing module configured to detect a soot loading on the sensing element of the particulate matter sensor and generate a regeneration request indicating a desired regeneration temperature. The system also includes a heating module configured to receive the regeneration request and send a heating command signal to the heating element based on the regeneration request and an electrical resistance module configured to detect an electrical resistance in the heating element. The system further includes a calibration module configured to determine an actual temperature of the heating element based on a resistance-to-temperature response model and a temperature feedback module configured to modify the heating command signal according to the difference between the desired regeneration temperature and the actual temperature.

The signal adjustment module may be configured to convert the heating command signal to an adjusted heating command signal that delivers the same net power to the heating element as the power delivered to the heating element by the (original) heating command signal. In one embodiment, the response voltage in the heating element has a steady-state portion. In one implementation, the adjusting heating command signal includes pulse width modulation and the pulses, at least the pulses for which the response voltage is being measured, may have a duty cycle of at least 30%. The calibration module may include a thermistor sub-module configured to generate a resistance-to-temperature response model based on known temperature conditions of a heating element and an exhaust calibration sub-module configured to adjust the resistance-to-temperature response model based on dynamic exhaust flow information.

Still further, the present disclosure relates to a method for generating a resistance-to-temperature model for a thermistor heating element of a particulate matter sensor. The method includes collecting electrical resistance data when a thermistor heating element of a particulate matter sensor is at a known temperature condition and generating a resistance-to-temperature model for the thermistor heating element based on the electrical resistance data. In another embodiment, the known temperature condition may be a temperature of the exhaust gas (or other component) upstream of the particulate matter sensor or the resistance-to-temperature model may be based on the ambient temperature upon engine 'key-on' or 'key-off'. In another embodiment, the method may include calibrating the resistance-to-temperature model to account for dynamic exhaust flow conditions. The method may be carried out one time upon initialization of an engine system or, in another embodiment, the method may be carried out periodically to re-calibrate the resistance-to-temperature model.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

Figure 1:
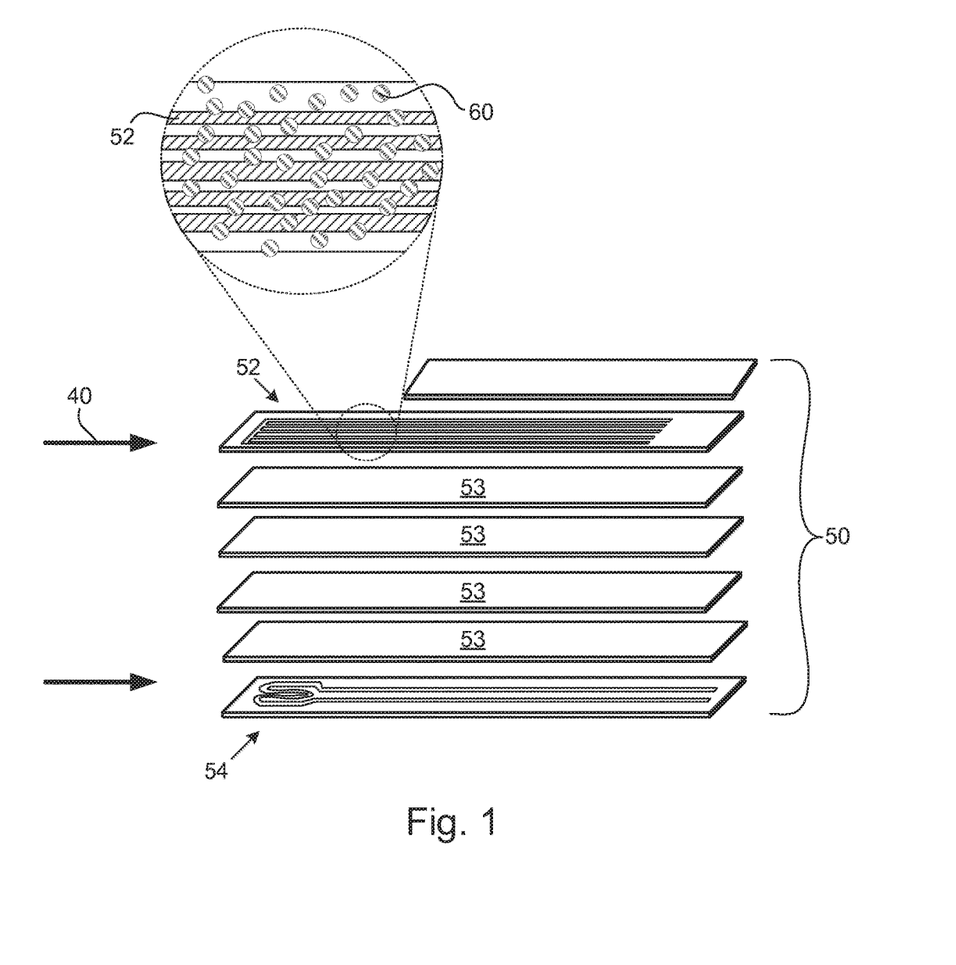
FIG. 1 is an exploded view of a particulate matter sensor with a magnified view of soot deposited across a sensing element, according to one embodiment.

FIG. 1 is an exploded view of a particulate matter sensor 50 with a magnified view of soot 60 deposited across a sensing element 52, according to one embodiment. The particulate matter sensor 50 includes a sensing element 52, various insulating plates or substrate layers 53, and a heating element 54. The sensing element is calibrated to detect a specific amount of particulate accumulation 60 on the sensor 50. Throughout the disclosure, the term 'soot' will be used to refer to any particulate matter, such as unburned hydrocarbons, present in the exhaust gas stream 40 that can be deposited onto the sensor 50. As soot 60 is deposited onto the sensing element 52, the electrical resistance 132 across the sensing element 52 decreases because the deposited soot 60 particles create shorts in the conductive wire pattern of the sensing element 52. When a certain amount of soot 60 has been deposited onto the sensing element 52, as indicated by a certain decrease in electrical resistance 132, a regeneration procedure may be triggered to remove the soot 60. The circular soot 60 particles depicted in FIG. 1 are included to show the general operation of the particulate sensor 50 and are not intended as actual depictions of soot particles 60.

The particulate matter sensor 50 may be able to self-regenerate by transmitting a heating command signal to a heating element 54. As the temperature of the sensor 50 increases, the soot 60 particles are oxidized and removed from the sensing elements 52. As particles 60 are removed, the resistance across the sensing elements 52 increases again and the heating element can decrease its thermal energy output once the electrical resistance 132 rises back up to a selected level, according to one embodiment. The particulate matter sensor 50 may include a multi-layered structure comprising the sensing element 52, multiple substrates or layers 53, and the heating element 54. The sensing element 52 may include electrodes constructed from electrically conductive materials or metals, such as, gold, platinum, osmium, rhodium, iridium, ruthenium, aluminum, titanium, zirconium, and the like, as well as, oxides, cermets, alloys, and combinations comprising at least one of the foregoing or other metals. Each sensing electrode may be made from the same or different material as the other sensing electrode(s).

The particulate matter sensor 50 may further include various substrates 53 that are useful in electrically isolating and protecting the sensing element 52 and the heating element 54 from the temperature surrounding the sensor and/or from the thermal reduction of the condensed particulates during a self-regeneration cycle. The substrates 53 may include, but are not limited to, an electrode protective layer, an electrode substrate, an isolation layer, an insulating temperature substrate, a heater substrate, insulating substrates. Generally, in some implementations, the number of insulating substrates is sufficient to prevent disruptive ionic or electrical communication between the heating element and the sensing electrode. The insulating substrates 53 may include non-ionically conducting, electrically insulating materials, such as alumina, zirconia, yttria, lanthanum oxide, silica, and combinations comprising at least one of the foregoing materials, or any like material capable of inhibiting electrical communication and providing physical protection. Although the composition of the individual substrates can vary, preferably the substrates are made from materials having substantially similar coefficients of thermal expansion, shrinkage characteristics, and chemical compatibility in order to minimize, if not eliminate, deformation and other processing problems. Additionally, the sensing element 52 and the heating element 54 may have various leads responsible for electrically coupling the elements with other components, such as controller modules and power sources.

Figure 2:
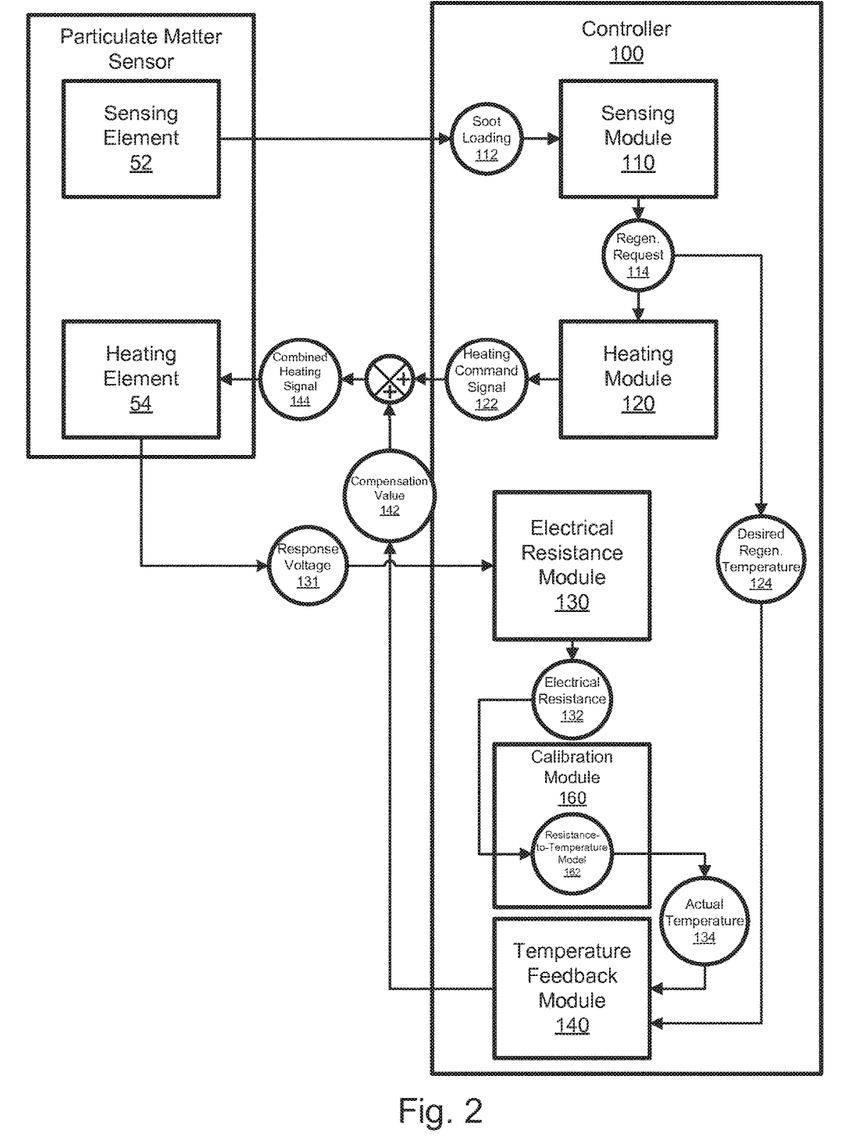
FIG. 2 is a schematic block diagram of a particulate matter regeneration system that includes a controller apparatus for regenerating a particulate matter sensor, according to one embodiment.

FIG. 2 is a schematic block diagram of a controller or controller apparatus 100 for regenerating a particulate matter sensor 50, according to one embodiment. The depicted controller apparatus 100 includes a sensing module 110, a heating module 120, an electrical resistance module 130, a calibration module 160, and a temperature feedback module 140.

The sensing module 110 communicates with the sensing element 52 and receives data corresponding to a soot loading 112 of the sensing element 52. In one embodiment, the soot loading 112 includes electrical resistance data that indicates a certain loading or accumulation of soot on the sensing elements 52. In another embodiment, the soot loading 112 includes capacitance data relating to the electrical capacitance of the sensing elements 52 with the deposited soot 60. When the soot loading 112 has reached a predetermined threshold level, the sensing module 110 may generate a regeneration request 114 that is sent to the heating module 120. For example, the particulate matter sensor 50 can apply a voltage between the electrodes of the sensing element 52. In response to the applied voltage, electrical current flows through the electrodes and any soot 60 deposited between the electrodes changes the resistivity level between the electrodes. Based on this change in resistance, the sensing module can convert the soot loading 112 into a regeneration request 114. For example if the sensing module 110 determines that a certain threshold of soot 60 has been deposited onto the sensor 50, the sensing module 110 may trigger a regeneration procedure to be implemented by the heating module 120.

The heating module 120 receives the regeneration request 114 and sends out a heating command signal 122 to the heating element 54. The heating command signal 122, in one embodiment, may specify a certain voltage or electrical current to be applied to the heating element 54 in order to heat the sensor 50 to a target/desired regeneration temperature 124. The target/desired regeneration temperature 124 is also sent to the temperature feedback module 140, described below, for comparison with an actual temperature 134 of the particulate matter sensor 50. In one embodiment, the heating command signal 122 may go directly (not depicted) to the heating element 54. In another embodiment, the voltage or electrical current specified by the heating command signal 122 may be supplemented by a heating command compensation value 142 to generate a combined heating command signal 144 that is sent to the heating element 54. Details regarding the delta heating command compensation value 142 and the combined heating command signal 144 are included below with reference to FIG. 3. The heating command signal 122 may also include timing and pulse width modulation parameters, as described below with reference to FIGS. 3, 5, and 6.

The electrical resistance module 130 is configured to detect the electrical resistance 132 across the heating element 54 and generate an approximation of the actual temperature of the heating element 54, which is represented by the actual temperature 134. Thus, the electrical resistance module 130 uses a real-time response voltage and current 131 across the heating element 54 to calculate the electrical resistance 132 of the heating element 54. Based on the calculated resistance, the calibration module 160 can approximate the actual temperature 134 of the heating element 54 using a resistance-to-temperature model 162 and can send the actual temperature 134 to the temperature feedback module 140 for comparison with the desired regeneration temperature 124. Additional details regarding the calibration module 160 and how the resistance 132 is converted to a temperature 134 are included below with reference to FIG. 8.

Figure 3:
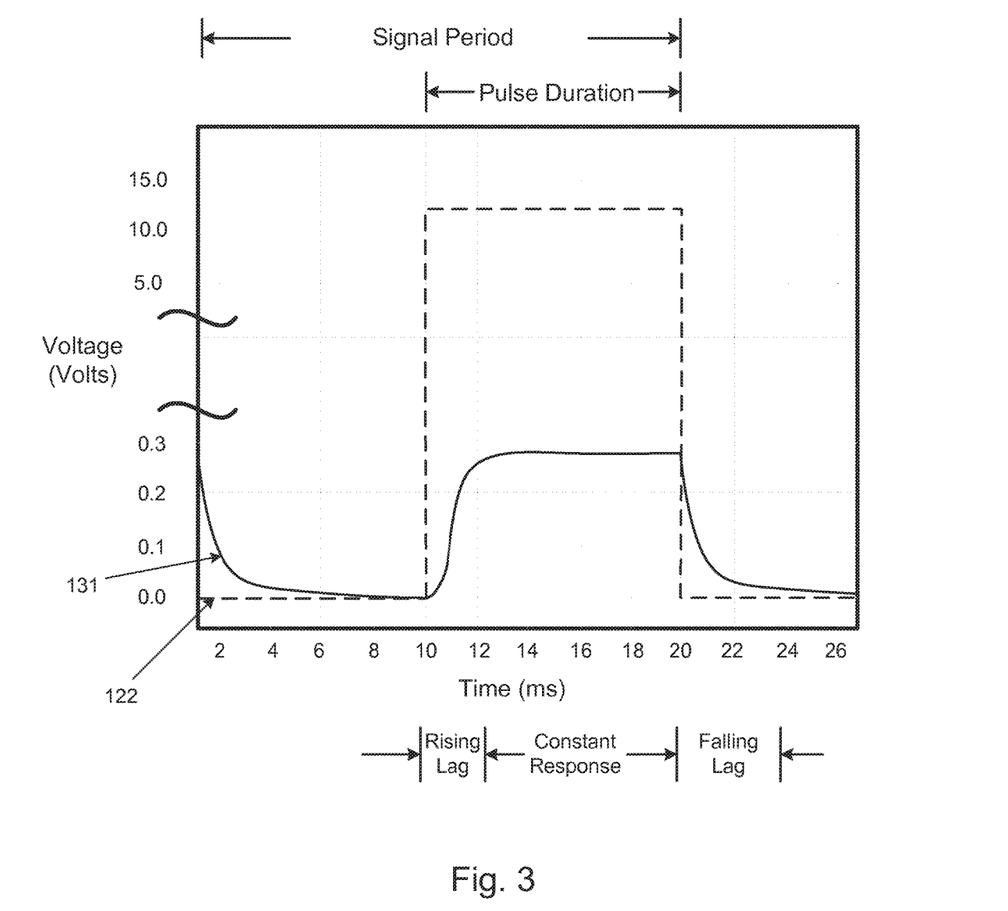
FIG. 3 is a graph showing a heating command signal and a heating element response, according to one embodiment.

FIG. 3 is a graph showing a heating command signal 122 and a heating response voltage 131, according to one embodiment. The graph has voltage on the y-axis and time, in milliseconds (ms), on the x-axis. The exact voltage values depicted in the graphs are illustrative only and are not intended to limit the scope of the present disclosure. Accordingly, the graphs have been included in the present disclosure in order to generally explain the pulse width modulation technique for controlling the response voltage 131 across the heating element 54. Additionally, the exact time values displayed across the x-axis are illustrative of a specific embodiment and are not intended to limit the scope of the disclosure. Certain applications will involve voltage and timing parameters that have different values. Also, different heating elements 54 will have different response dynamics and, therefore, the voltage response 131 line is only illustrative of one embodiment and heating elements made from different materials may respond differently and have different lag times.

Many applications have a direct current, fixed voltage source (e.g., car battery). Therefore, one way of controlling the amount of power delivered in a direct current, fixed voltage environment is via pulse width modulation. Pulse width modulation involves turning a switch, between the supply and the load, on and off repeatedly to deliver a desired power to the load from a fixed supply. In the graph depicted in FIG. 3, the dotted line represents the heating command signal 122 sent to the heating element 54 and the solid line represents the voltage response 131 of the heating element 54. As depicted, the response voltage 131 across the heating element does not exactly line up with the heating command signal 122. The response voltage 131 shows both a rising and a falling lag time. During these lag times, the response voltage 131 is not constant and any electrical resistance calculations based on the response voltage 131 does not accurately reflect the condition of the heating element 54. Accordingly, the electrical resistance module 130 may be calibrated to only use response voltage 131 data when the response voltage is constant (or at least substantially constant). However, in certain embodiments, the heating command signal 122 implements a series of rapid voltage pulses and the response voltage 131 never reaches a steady-state/constant response. Such a situation is described below with reference to FIGS. 5 and 6. Once the response voltage 131 has been received/detected, the electrical resistance module 130 calculates the electrical resistance across the heating element and approximates the actual temperature 134 of the heating element 54 based on the electrical resistance. The actual temperature 134 is then sent to the temperature feedback module 140.

Referring back to FIG. 2, the temperature feedback module 140 is configured to compare the actual temperature 134 with the targeted/desired regeneration temperature 124. For example, in one embodiment, the desired regeneration temperature 124 may be 750° C. but the actual temperature 134 may only be 550° C. In this example, the temperature feedback module 140 would report a positive heating command compensation value 142 that corresponds with the 200° C. difference (i.e., the error). In other words, the heating command compensation value 142 may be an addition or a subtraction from the default heating command signal 122. Once the default heating command signal 122 and the heating command compensation value 142 have been summed (see the summation block in FIG. 2), the resultant command is the combined heating command signal 144 and it is passed to the heating element 54. Although not depicted, the controller apparatus 100 may also include other conventional temperature feedback control components, such as value reset modules, value recording modules, and error integration/derivation ("PID") parameters.

Figure 4:
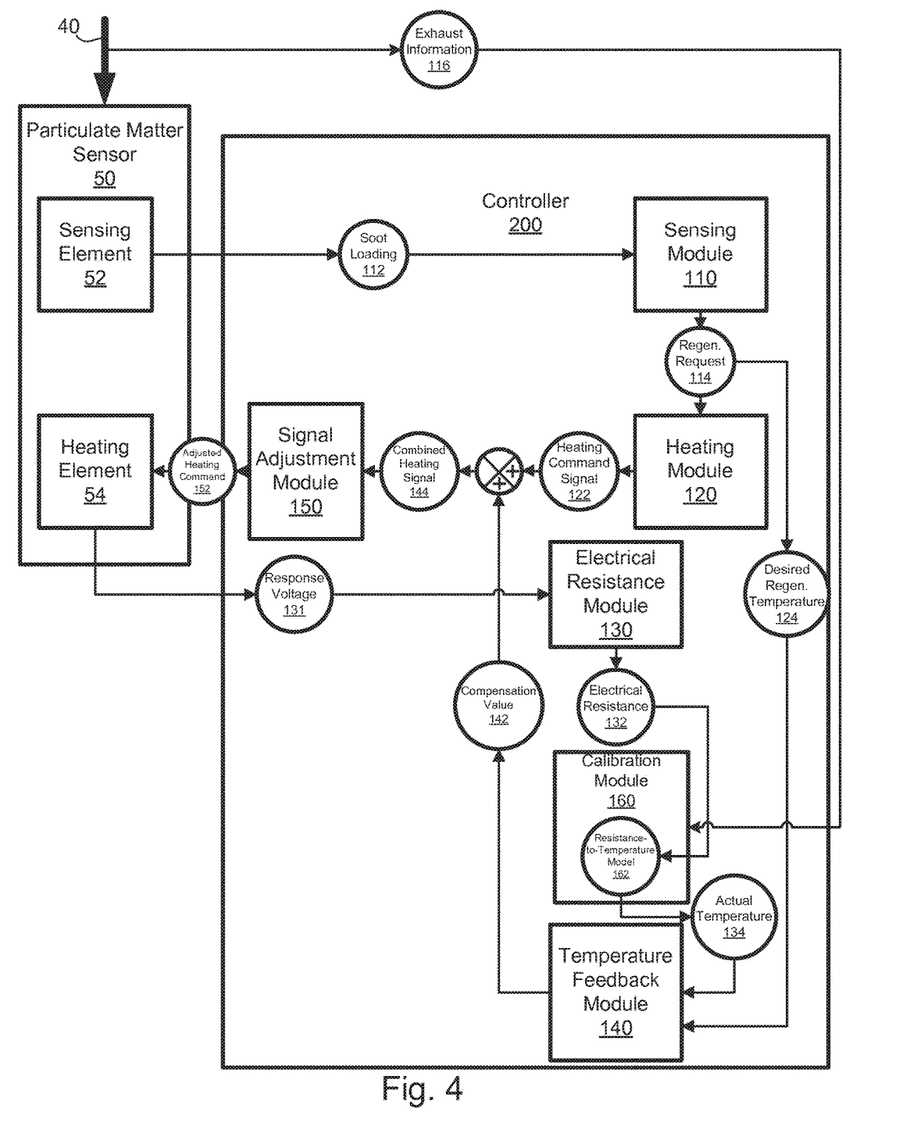
FIG. 4 is a schematic block diagram of a particulate matter regeneration system that includes a controller apparatus for regenerating a particulate matter sensor, according to another embodiment.

FIG. 4 is a schematic block diagram of another controller apparatus 200 for regenerating a particulate matter sensor 50, according to one embodiment. The controller apparatus 200 depicted in FIG. 4 includes the modules described above and one additional module, the signal adjustment module 150. Depending on the parameters of the combined heating command signal 144, the signal adjustment module 150 may change the pulse width modulation parameters and generate an adjusted heating command signal 152 in order to improve the accuracy and reliability of the response voltage 131 detected across the heating element 54. Details regarding this adjustment module 150 are included below with reference to FIGS. 5 and 6.

Also depicted in FIG. 4 is an exhaust stream 40 in fluid contact with the particulate matter sensor 50. The sensing module 110 may detect dynamic exhaust flow information 116, such as real-time temperature, pressure, flow-rate, etc., and may incorporate the exhaust flow information 116 into the regeneration request 114 sent to the heating module 120. For example, if the exhaust flow 40 temperature is already at or near the desired regeneration temperature 124, the sensing module 110 may not send a regeneration request 114 and because no active regeneration is required. Further, if the exhaust flow 40 temperature is low, the regeneration request 114 may pass along such data to the heating module 120 so that the heating module 120 can compensate for the colder exhaust temperatures.

Figure 5:
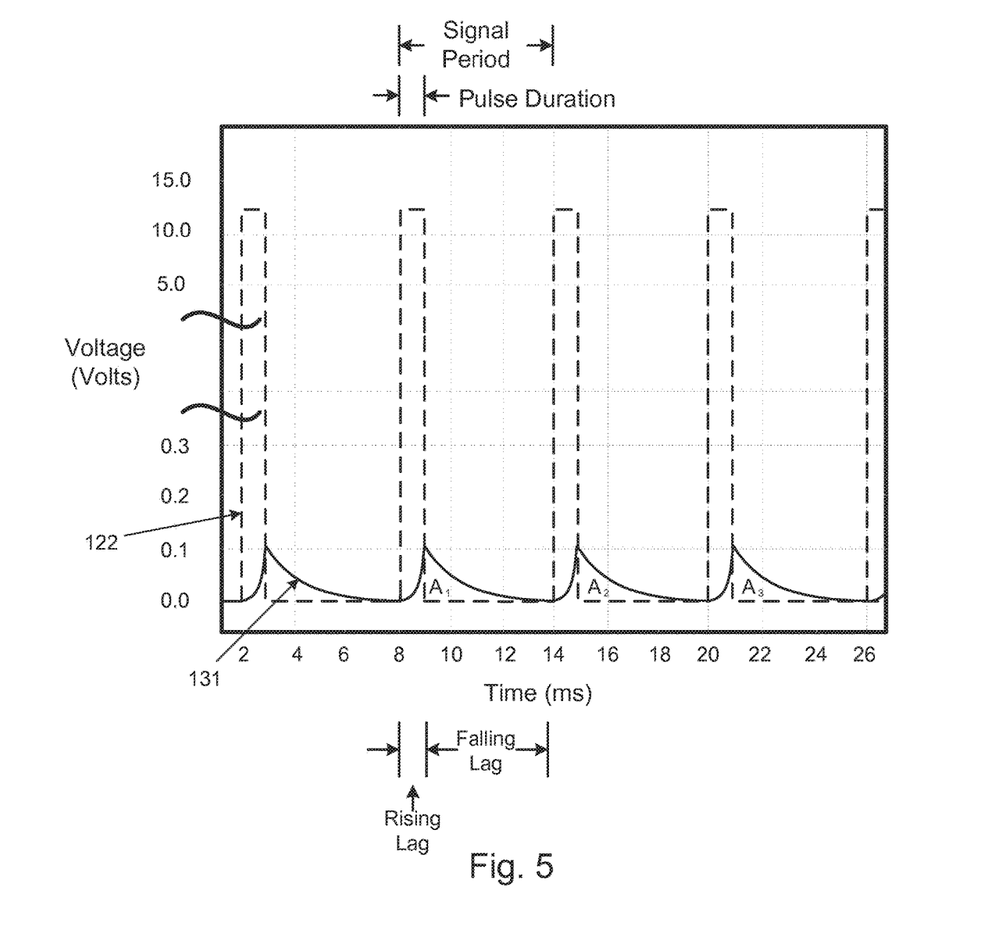
FIG. 5 is a graph showing a heating command signal and a heating element response, according to one embodiment.

FIG. 5 is a graph showing a heating command signal 122, 144 and a voltage response 131, according to one embodiment. The graph has voltage on the y-axis and time, in milliseconds (ms), on the x-axis. The exact voltage values depicted in the graphs are illustrative only and are not intended to limit the scope of the present disclosure. Accordingly, the graphs have been included in the present disclosure in order to generally explain the pulse width modulation technique for controlling the response voltage 131 across the heating element 54. Additionally, the exact time values displayed across the x-axis are illustrative of one specific embodiment and are not intended to limit the scope of the disclosure. Certain applications will involve voltage and timing parameters that have different values. Additionally, different heating elements 54 will have different response dynamics and, therefore, the voltage response 131 line is only illustrative of one embodiment and other materials may respond differently and have different lag times.

FIG. 5 shows a heating command signal 122 and a voltage response 131 in the absence of a signal adjustment module 150. The graph shows a series of narrow voltage pulses 122. The voltage response 131 from these pulses does not reach a constant value during the pulse. In other words, the response voltage 131 only comprises a rising lag portion and a falling lag portion and the response is not constant. In this situation, when the pulse duration is too short to allow for a constant voltage response 131, any resistance calculations (and subsequent temperature calculations) would be inaccurate and would not adequately reflect the condition of the heating element 54. In order to improve the accuracy of the calculated resistance and temperature 134 of the heating element 54, the heating command signal 122 can be controlled to lengthen the pulse duration, thereby allowing the response voltage 131 to reach a constant value, while still delivering the same net heating power to the heating element 54.

Figure 6:
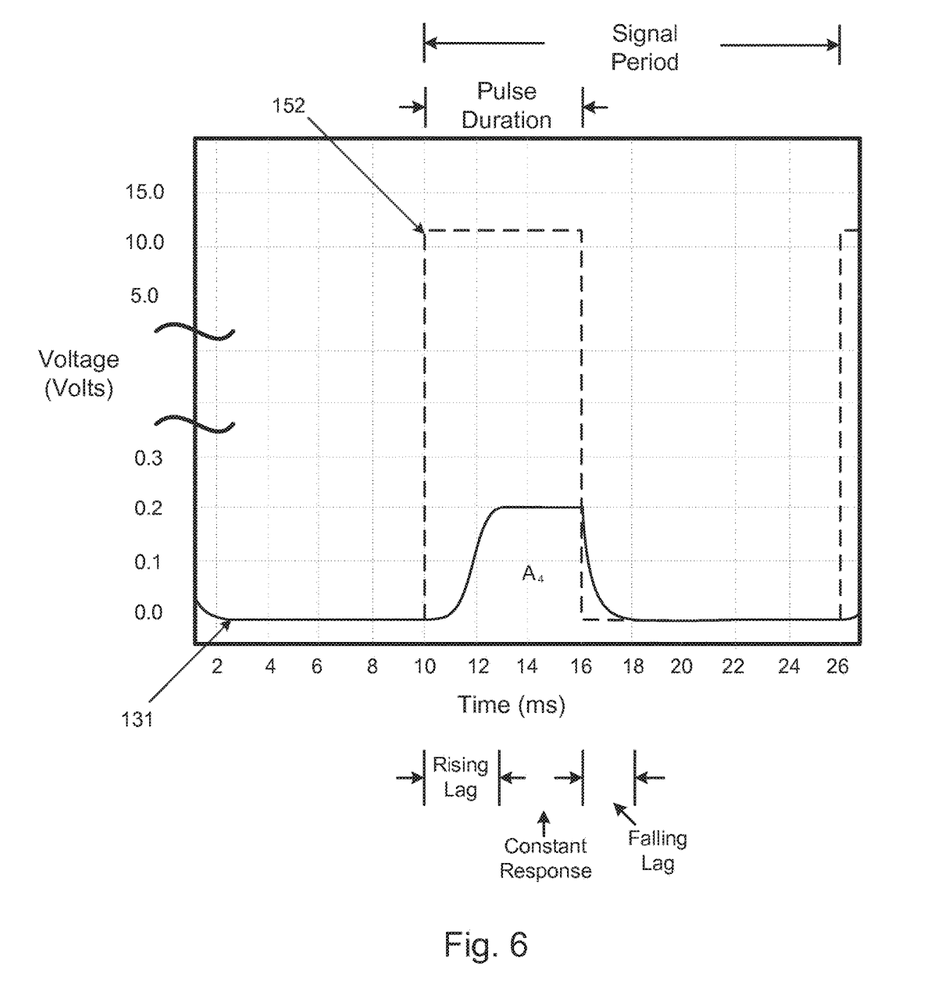
FIG. 6 is a graph showing an adjusted heating command signal and an adjusted heating element response, according to one embodiment.

FIG. 6 is a graph showing an adjusted heating command signal 152 and a voltage response 131, according to one embodiment. The signal adjustment module 150 can alter the standard heating command signal 122, 144 and produce an adjusted heating command signal 152 that both allows the response voltage to reach steady-state and delivers the proper heating power to the heating element 54. In FIG. 5, three areas below the voltage response curve 131 are labeled $A_1$, $A_2$, and $A_3$. These areas correspond to the power delivered to the heating element 54. The signal adjustment module 150 can convert the combined heating command signal 144 into an adjusted heating command signal 152 that delivers the same power to the heating element 54 as three of the narrow pulses from FIG. 5. In FIG. 6, the area below the voltage response curve 131 is labeled $A_4$, which represents an area equal to the combined area of $A_1$, $A_2$, and $A_3$. Thus, the net power delivery of the one pulse in FIG. 6 is substantially equal to the power delivery of three of the pulses in FIG. 5. Therefore, the signal adjustment module 150 can alter the pulse duration and the signal period of the heating command signal sent to the heating element 54 in order to satisfy two criteria. First, the same net power should be delivered with the adjusted heating command signal 152 as would be delivered with the combined heating command signal 144. Second, at least a portion of the voltage response 131 from the adjusted heating command signal 152 should be substantially constant to allow for an accurate resistance calculation and an accurate temperature approximation. In one embodiment, the duty cycle (pulse duration as a percentage of the signal period) of the adjusted heating command signal 152 is at least 30%.

Figure 7:
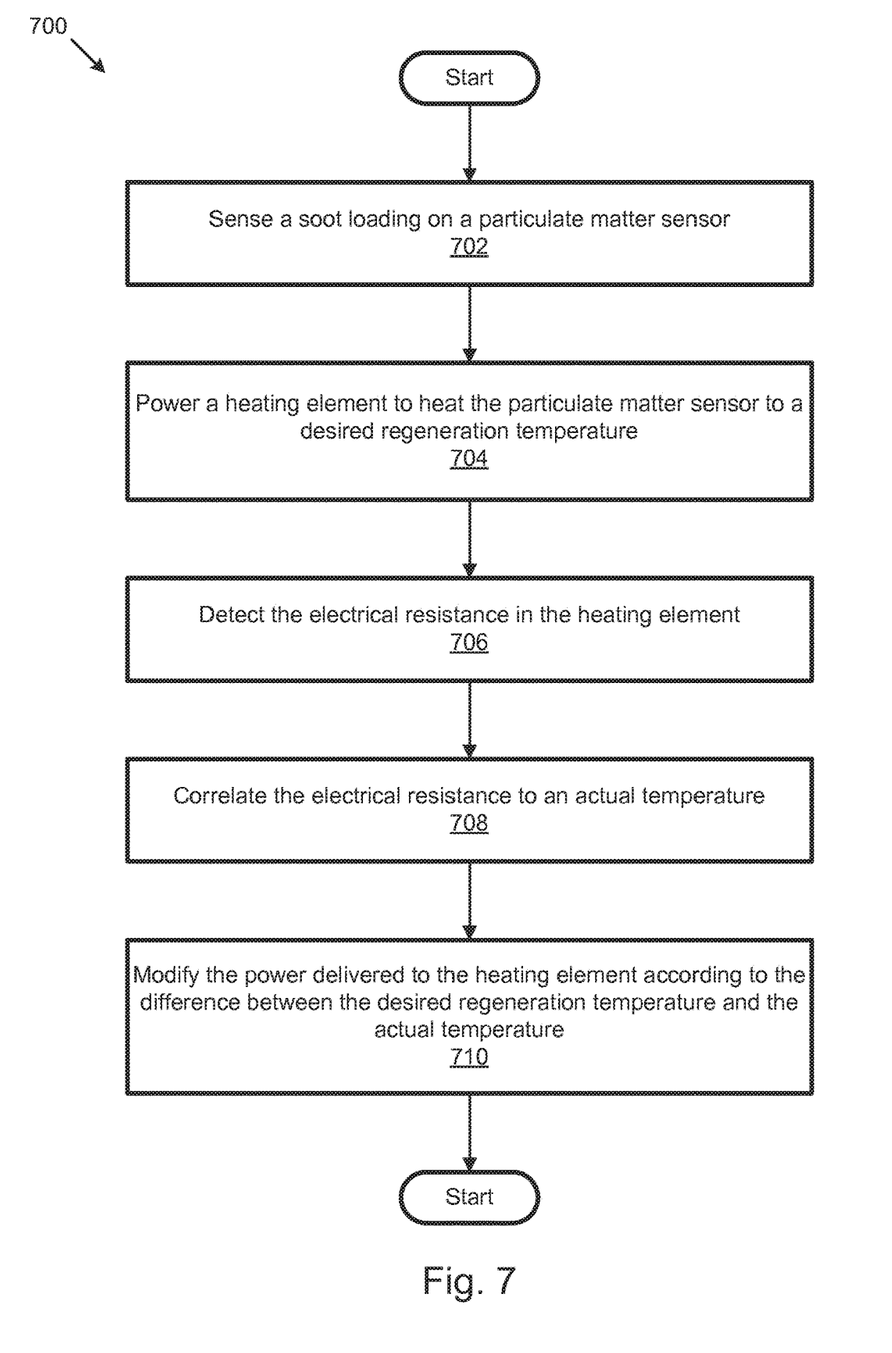
FIG. 7 is a schematic flow chart diagram of a method for regenerating a particulate matter sensor, according to one embodiment.

FIG. 7 is a schematic flow chart diagram of a method 700 for regenerating a particulate matter sensor 50, according to one embodiment. The method 700 includes sensing a soot loading on a particulate matter sensor at 702. The method 700 further includes powering a heating element to heat the particulate matter sensor to a desired regeneration temperature to oxidize at least a portion of the soot loading at 704. Also, the method 700 includes sensing a response voltage in the heating element at 706 and correlating the response voltage of the heating element to an actual temperature of the heating element at 708. Additional details relating to how the response voltage and the electrical resistance are converted into a temperature are included below with reference to FIG. 8. Still further, the method 700 includes adjusting the power delivered to the heating element according to the difference between the desired regeneration temperature and the actual temperature of the heating element at 710.

Figure 8:
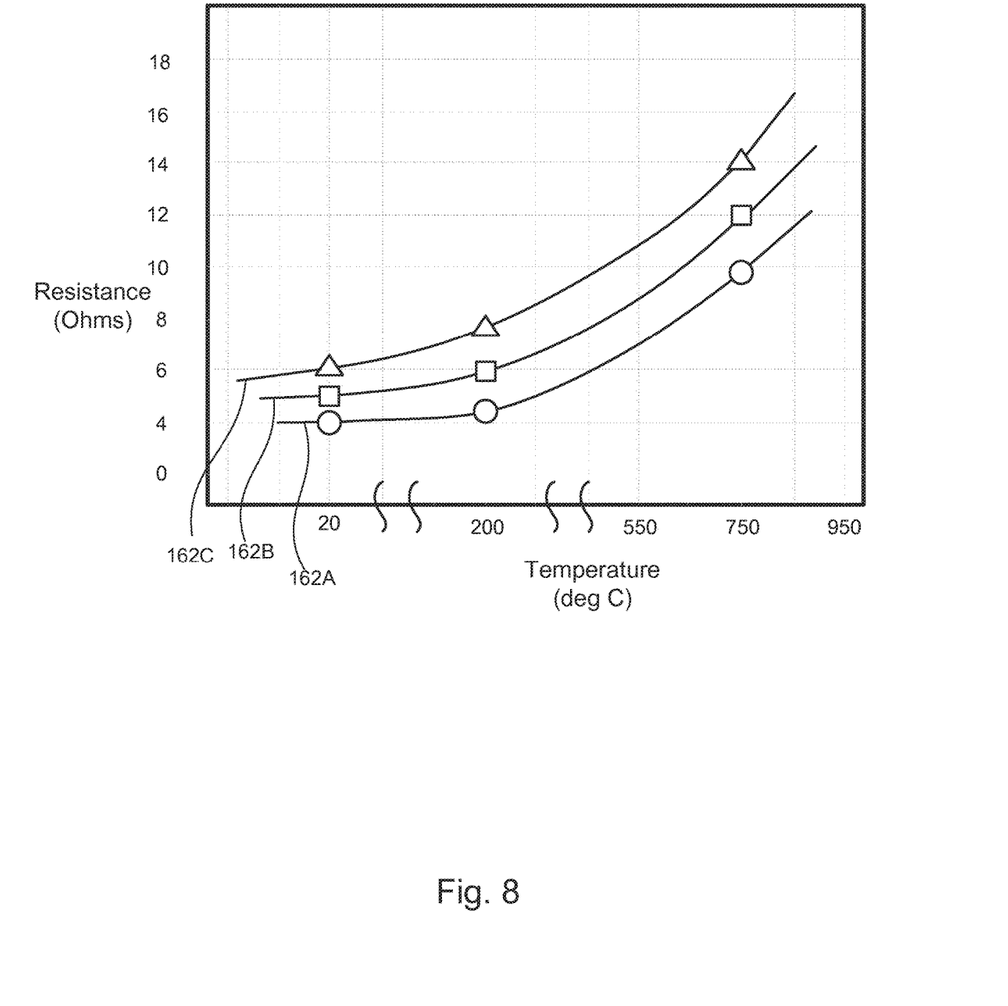
FIG. 8 is a graph showing three different resistance-to-temperature models, according to one embodiment.

FIG. 8 is a graph showing three different resistance-to-temperature models 162A, 162B, 162C, according to one embodiment. The graph has electrical resistance on the y-axis and temperature, on the x-axis. The exact values depicted in the graph are illustrative only and are not intended to limit the scope of the present disclosure. Accordingly, FIG. 8 has been included in the present disclosure in order to generally explain the generation of resistance-to-temperature models 162. Additionally, different heating elements 54 will have different response dynamics and, therefore, the resistance-to-temperature models are only illustrative of one embodiment and other materials may respond differently.

As briefly mentioned above, and as depicted in FIGS. 2 and 4, the calibration module 160 is configured to receive the measured electrical resistance 132 from the electrical resistance module 130 and determine the actual temperature 134 of the heating element 54. However, the actual temperature 134 of the heating element 54 is dependent on the material of the heating element 54 and the dynamic exhaust flow information 116. Thus, a single resistance-to-temperature curve may not accurately reflect the temperature/resistance correlation of every engine system. Therefore the calibration module 160 is configured to also determine an accurate resistance-to-temperature model 162 based upon the specifics of a given application.

As seen in FIG. 8, different thermistor materials may have different temperature/resistance correlations. For example, a thermistor heating element made from a certain metal may have a different temperature/resistance correlation than a thermistor heating element made from a different material. In another embodiment, the thermistor heating element material may be the same but, due, to part-to-part variation (perhaps caused by manufacturing procedures), each heating element 54 has a different temperature/resistance correlation. Accordingly, although not schematically depicted in the block diagrams, the calibration module 160 can detect electrical resistance data from the heating element 54 when the temperature of the heating element 54 is known. For example, when turning on a vehicle after the vehicle has been turned off for a period of several hours (e.g., overnight), the temperature of the heating element is essentially room temperature and the calibration module 160 can detect the resistance of the heating element 54 at the know temperature and plot that data point on a response curve. In other situations where the exhaust gas has been at a known temperature for a certain time (e.g., idle), the calibration module 160 can once again detect the resistance across the heating element 54 and plot the data point, thus generating a temperature response curve (i.e., a resistance-to-temperature model 162).

FIG. 8 shows three different resistance-to-temperature models 162A, 162B, 162C as an example of how different heating elements 54 can have different temperature/resistance correlations. The first resistance-to-temperature model 162A, shown with the circular data points, is an example of a comparatively lower resistance model. The second resistance-to-temperature model 162B, shown with the rectangular data points, may represent an average or a nominal resistance/temperature correlation and the third resistance-to-temperature model 162C, shown with the triangular data points, may represent a high limit resistance/temperature correlation. These models 162A, 162B, 162C are not intended to limit the present disclosure. For example, the models may each include many data points over many different temperatures. In another embodiment, the models may only need a single data point in order to determine the correlation.

In a further embodiment, the calibration module 160 may be configured to also consider the exhaust flow dynamics when generating the resistance-to-temperature model 162. For example, depending on the flow rate and temperature of the exhaust gas stream 40, the accuracy of the model 162 may be affected. Therefore, the calibration module 160 may also include adjustments and/or modifications according to the detected exhaust flow dynamics 116.

Figure 9:
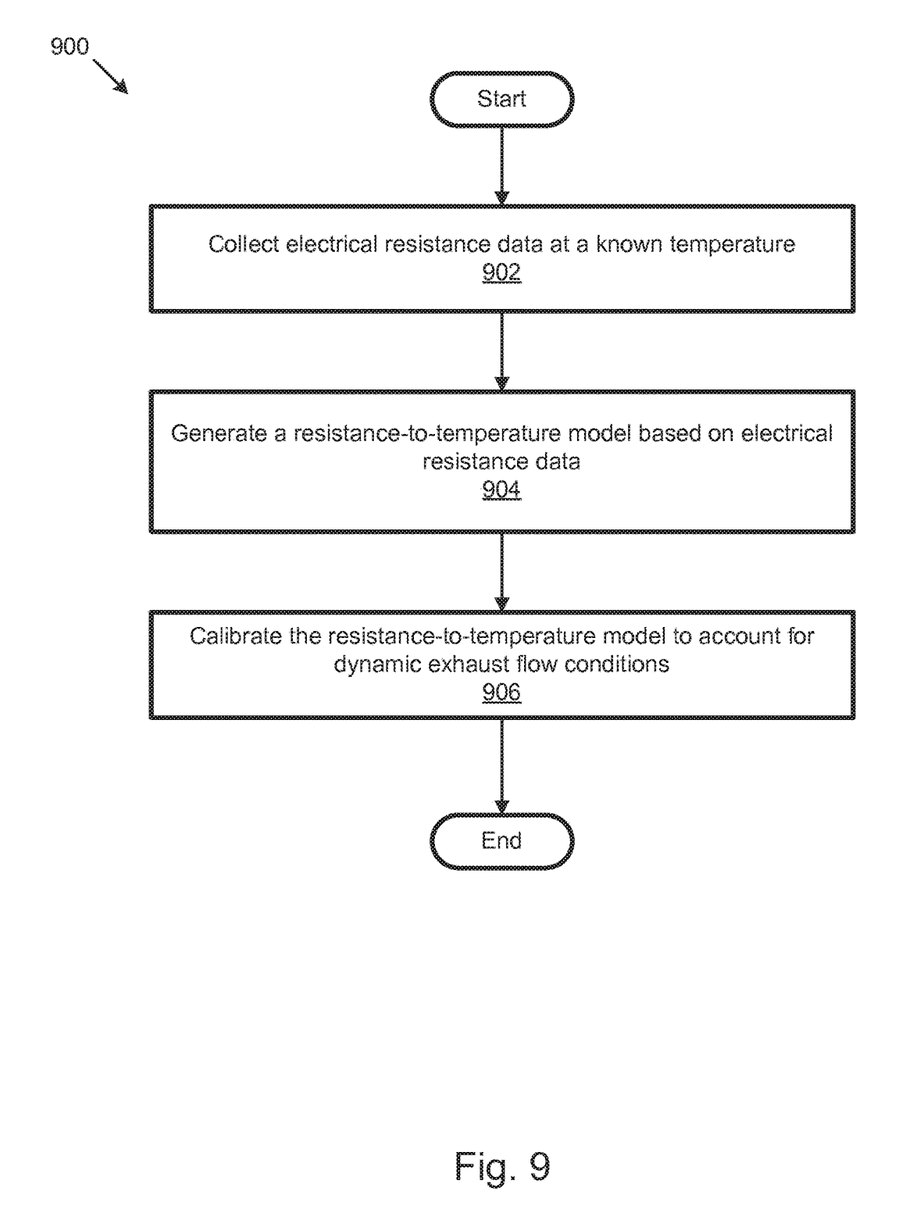
FIG. 9 is a schematic flow chart diagram of a method for generating a resistance-to-temperature model for a thermistor heating element of a particulate matter sensor.

FIG. 9 is a schematic flow chart diagram of a method 900 for generating a resistance-to-temperature model 162 for a thermistor heating element 54 of a particulate matter sensor 50. The method first includes collecting electrical resistance data when a thermistor heating element of a particulate matter sensor is at a known temperature condition at 902. The method 900 further includes generating a resistance-to-temperature model for the thermistor heating element based on the electrical resistance data at 904. The method 900 may also include calibrating the resistance-to-temperature model to account for dynamic exhaust flow information at 906. The calibration module 160 may be configured to perform the steps of the method 900 a single time or the steps of the method 900 may be occasionally or periodically performed. For example, the collecting 902 and generating 904 steps may be performed a single time during the initialization (i.e., fabrication) of the engine system and the calibrating step 906 may be performed periodically as real-time exhaust flow information 116 is made available. In another embodiment, all the steps of the method 900 may be periodically performed by the calibration module 160 in order to re-calibrate or re-adjust the resistance-to-temperature model 162.

Reference throughout this specification to "one embodiment," "an embodiment," or similar language means that a particular feature, structure, or characteristic described in connection with the embodiment is included in at least one embodiment of the subject matter of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the subject matter of the present disclosure, however, absent an express correlation to indicate otherwise, an implementation may be associated with one or more embodiments.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of computer readable program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of computer readable program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the computer readable program code may be stored and/or propagated on in one or more computer readable medium(s).

The computer readable medium may be a tangible computer readable storage medium storing the computer readable program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store computer readable program code for use by and/or in connection with an instruction execution system, apparatus, or device.

The computer readable medium may also be a computer readable signal medium. A computer readable signal medium may include a propagated data signal with computer readable program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport computer readable program code for use by or in connection with an instruction execution system, apparatus, or device. Computer readable program code embodied on a computer readable signal medium may be transmitted using any appropriate medium, including but not limited to wireless, wireline, optical fiber cable, Radio Frequency (RF), or the like, or any suitable combination of the foregoing In one embodiment, the computer readable medium may comprise a combination of one or more computer readable storage mediums and one or more computer readable signal mediums. For example, computer readable program code may be both propagated as an electro-magnetic signal through a fiber optic cable for execution by a processor and stored on RAM storage device for execution by the processor.

Computer readable program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The computer readable program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present subject matter may be embodied in other specific forms without departing from its spirit or essential characteristics. The described embodiments are to be considered in all respects only as illustrative and not restrictive.

What is claimed is:

1. A system for generating a resistance-to-temperature model and regenerating a particulate matter sensor, comprising:
   a particulate matter sensor having a heating element; and
   a controller coupled to an engine, the controller including:
   a sensing circuit configured to detect a soot loading on the particulate matter sensor and generate a regeneration request indicating a desired regeneration temperature,
   a heating circuit configured to receive the regeneration request, generate a heating command signal based on the regeneration request, and send the heating command signal to the heating element of the particulate matter sensor based on the regeneration request,
   an electrical resistance circuit configured to detect an electrical resistance of the heating element,
   a calibration circuit configured to generate a resistance-to-temperature model for the heating element based on electrical resistance data collected by the electrical resistance circuit at known temperatures and to determine an actual temperature of the heating element during heating of the particulate matter sensor based on the generated resistance-to-temperature model and the detected electrical resistance, and
   a temperature feedback circuit configured to modify the heating command signal according to a difference between the desired regeneration temperature and the actual temperature of the heating element during heating of the particulate matter sensor.

2. The system of claim 1, wherein the calibration circuit is configured to generate the resistance-to-temperature model at a single time for the heating element based on electrical resistance data collected by the electrical resistance circuit at known temperatures.

3. The system of claim 1, wherein the electrical resistance data is periodically collected to re-generate the resistance-to-temperature model.

4. The system of claim 1, wherein the calibration circuit is further configured to calibrate the resistance-to-temperature model based on dynamic exhaust flow conditions.

5. The system of claim 4, wherein the calibrating is performed periodically responsive to real-time exhaust flow information.

6. The system of claim 1, wherein the electrical resistance is detected by measuring a response voltage of the heating element during heating of the particulate matter sensor and converting the response voltage into the electrical resistance.

7. The system of claim 6, further comprising a signal adjustment circuit configured to convert the heating command signal to an adjusted heating command signal, wherein the response voltage in the heating element has a steady-state portion.

8. A system for generating a resistance-to-temperature model, comprising:
   a particulate matter sensor having a heating element; and
   a controller coupled to an engine, the controller including:
      an electrical resistance circuit configured to collect electrical resistance data when the heating element of the particulate matter sensor is at known temperature conditions, and
      a calibration circuit configured to generate a resistance-to-temperature model for the heating element based on the electrical resistance data collected by the electrical resistance circuit at known temperatures.

9. The system of claim 8, wherein the calibration circuit is configured to generate the resistance-to-temperature model at a single time for the heating element based on electrical resistance data collected by the electrical resistance circuit at known temperatures.

10. The system of claim 8, wherein the electrical resistance data is periodically collected to re-generate the resistance-to-temperature model.

11. The system of claim 8, wherein the calibration circuit is further configured to calibrate the resistance-to-temperature model based on dynamic exhaust flow conditions.

12. The system of claim 11, wherein the calibrating is performed periodically responsive to real-time exhaust flow information.

13. The system of claim 8, wherein the electrical resistance is detected by measuring a response voltage of the heating element during heating of the particulate matter sensor and converting the response voltage into the electrical resistance.

14. A method for generating a resistance-to-temperature model for a thermistor heating element of a particulate matter sensor, comprising:
   collecting electrical resistance data when a thermistor heating element of a particulate matter sensor is at a known temperature condition;
   generating a resistance-to-temperature model for the thermistor heating element based on the electrical resistance data; and
   calibrating the resistance-to-temperature model to account for dynamic exhaust flow conditions.

15. The method of claim 14, wherein the calibrating is performed periodically responsive to real-time exhaust flow information.

16. A method for generating a resistance-to-temperature model for a thermistor heating element of a particulate matter sensor, comprising:
   collecting electrical resistance data when a thermistor heating element of a particulate matter sensor is at a known temperature condition; and
   generating a resistance-to-temperature model for the thermistor heating element based on the electrical resistance data, wherein the method is carried out one time upon initialization of an engine system.

17. A method for generating a resistance-to-temperature model for a thermistor heating element of a particulate matter sensor, comprising:
   collecting electrical resistance data when a thermistor heating element of a particulate matter sensor is at a known temperature condition; and
   generating a resistance-to-temperature model for the thermistor heating element based on the electrical resistance data, wherein the method is carried out periodically to re-calibrate the resistance-to-temperature model.

18. The method of claim 17, wherein collecting the electrical resistance data comprises detecting a resistance across the thermistor heating element.

19. The method of claim 18, wherein detecting the resistance is based on a real-time response voltage and current across the thermistor heating element.

* * * * *